(12) United States Patent
Beaumont

(10) Patent No.: US 7,488,317 B2
(45) Date of Patent: Feb. 10, 2009

(54) ELECTRO-EPILATION METHOD

(75) Inventor: Clément Beaumont, Ste-Foy (CA)

(73) Assignee: Dectronique (1984) Inc., Québec, Québec (CA)

( * ) Notice: Subject to any disclaimer, the term of this patent is extended or adjusted under 35 U.S.C. 154(b) by 551 days.

(21) Appl. No.: 11/243,993

(22) Filed: Oct. 6, 2005

(65) Prior Publication Data

US 2006/0149227 A1 Jul. 6, 2006

Related U.S. Application Data

(60) Provisional application No. 60/617,064, filed on Oct. 12, 2004.

(51) Int. Cl.
*A61B 18/18* (2006.01)
(52) U.S. Cl. .......................... 606/36; 606/44
(58) Field of Classification Search .................. 606/36, 606/43–44; 707/104.1
See application file for complete search history.

(56) References Cited

U.S. PATENT DOCUMENTS

| | | | |
|---|---|---|---|
| 3,651,812 A * | 3/1972 | Samuels ................... | 606/44 |
| 4,167,187 A | 9/1979 | Biagi | |
| 4,216,775 A | 8/1980 | Cottingham | |
| 4,321,926 A * | 3/1982 | Roge ...................... | 606/36 |
| 4,498,474 A | 2/1985 | Chalmers et al. | |
| 4,550,728 A * | 11/1985 | Runyon et al. ............ | 606/36 |
| 4,940,466 A | 7/1990 | Paduano et al. | |
| 5,169,398 A | 12/1992 | Glaros | |
| 5,727,560 A | 3/1998 | Ogura | |
| 6,059,777 A | 5/2000 | Acquaire | |
| 6,063,108 A | 5/2000 | Salansky et al. | |
| 6,080,146 A | 6/2000 | Altshuler et al. | |
| 6,234,969 B1 | 5/2001 | Chaintreuil et al. | |
| 6,267,780 B1 | 7/2001 | Streeter | |
| 6,280,396 B1 | 8/2001 | Clark | |
| 6,506,155 B2 | 1/2003 | Sluis | |
| 6,544,259 B1 | 4/2003 | Tsaliovich | |
| 6,607,523 B1 | 8/2003 | Asah et al. | |
| 6,620,158 B2 * | 9/2003 | Ronci ...................... | 606/36 |
| 2003/0130567 A1 | 7/2003 | Mault et al. | |
| 2004/0068255 A1 | 4/2004 | Short et al. | |
| 2004/0186466 A1 * | 9/2004 | Chornenky et al. ........ | 606/36 |
| 2006/0026205 A1 * | 2/2006 | Butterfield ............... | 707/104.1 |

FOREIGN PATENT DOCUMENTS

| | | |
|---|---|---|
| WO | WO97/28752 | 8/1997 |
| WO | WO2004042510 A2 | 5/2004 |

* cited by examiner

*Primary Examiner*—Michael Peffley
*Assistant Examiner*—Alex Helmboldt
(74) *Attorney, Agent, or Firm*—Ogilvy Renault LLP

(57) ABSTRACT

There is described a method of epilation using an insulated probe connected to an epilator apparatus supplying multiple pulses of energy that created concentrated heat at the probe tip. The steps of the method comprise inserting the probe tip into the hair follicle; positioning the probe tip at a position corresponding to either the bulb or the bulge; activating the apparatus to generate heat at the probe tip using predefined settings; and displacing the probe tip from the position to the other of the bulb and the bulge with continuous generation of heat using the multiple pulses of energy at the probe tip.

15 Claims, 4 Drawing Sheets

ELECTRO-EPILATION METHOD

CROSS-REFERENCE TO RELATED APPLICATIONS

This application claims priority under 35USC§119(e) of U.S. provisional patent application 60/617,064 filed Oct. 12, 2004, the specification of which is hereby incorporated by reference.

STATEMENT REGARDING FEDERALLY SPONSORED RESEARCH OR DEVELOPMENT

Not Applicable.

TECHNICAL FIELD

The present invention relates to the field of hair removal, and more particularly, to methods of permanently removing superfluous or unwanted hair by inserting a fine needle into the hair follicle and applying an electric current through the needle to destroy the hair root, or papilla, thereby removing the hair.

BACKGROUND OF THE INVENTION

Electrolysis is either of two electrical epilation methods for the permanent removal of human hair. A practitioner of electrolysis, as the term is used in epilation, is called an electrologist.

One method involves using a person's body as an electrolytic cell. This method is known as galvanic. The other method is known as thermolysis, RF, shortwave or diathermy. Galvanic and thermolysis are often combined in a method known as the BLEND™. All three of these methods use a metal probe 0.002 to 0.006 inches in diameter which is inserted into hair follicles to the depth of the dermal papilla or hair matrix, which is the site of formation of hair from highly mitotic and keratinized cells.

A galvanic epilator is essentially a positive ground power supply that delivers 0-3 mA through the body. The follicular probe is the cathode of an electrolytic cell. Sodium hydroxide formed at the cathode burns out the hair matrix cells. Modern galvanic epilators automatically adjust the voltage to maintain constant current.

A thermolytic epilator is essentially a radio transmitter, usually with an output of about 0-8 watts at a frequency of 13.56 MHz. RF energy emanates from the probe to tissue within about a few millimeters. The idea is to heat the hair matrix to about 48° C., causing electro-coagulation.

Thermolysis allows more epilations in less time, typically 1-4 seconds per insertion, compared to 15 seconds to several minutes for galvanic. On the other hand, the galvanic method is more thorough, and leaves fewer follicles capable of regrowing hair. The BLEND™ method combines RF and direct current, combining many of the advantages of both methods.

While Electrolysis has some very good results compared to other epilation techniques, it can be expensive, tedious, and painful for the patient. It can be difficult for large amounts of hair. If done improperly, it can result in partial to full regrowth, lasting skin damage, and spread of infection.

Therefore, there is a need for new methods and systems in the area of electro-epilation.

SUMMARY OF THE INVENTION

One aspect of the present invention is to provide a new method for electro-epilation that can be used with existing electro-epilation devices.

In accordance with this broad aspect of the present invention, there is provided a method of epilation using an insulated probe connected to an epilator apparatus supplying multiple pulses of energy that create concentrated heat at the probe tip. The steps of the method comprise inserting the probe tip into the hair follicle; positioning the probe tip at a position corresponding to either the bulb or the bulge; activating the apparatus to generate heat at the probe tip using predefined settings; and displacing the probe tip from the position to the other of the bulb and the bulge with continuous generation of heat using the multiple pulses of energy at the probe tip.

The heat generated by the probe is sufficient to create a concentrated coagulation only at the tip of the insulated probe to destroy at least some of the germinating cells responsible for hair growth.

This method may be used with a 27 MHz frequency to permanently and rapidly destroy all types of hair. In addition, the output radio wave circuitry delivers a very high power (22.5 Watts) which enables treatments in a very short timing of few thousandths of a second to coagulate in a very concentrated fashion the cells responsible for hair growth, thereby providing positive results.

The 27 MHz frequency also provides comfort for the patient. The current is so quick and so concentrated that treatments are comfortable.

The apparatus used with the method of the present invention meets the applicable international standards for radio frequency emissions, and is protected against external disturbances. Some selective filters may be implemented in a shielded cage to inhibit the harmonic frequency from emission.

A 16 bits Technology may be used in the apparatus, thereby enabling some special application techniques. Furthermore, at least 10 Operators may log-in to the system to access the 700 or more electro-epilation programs classified by body area and type of hair, which may be altered and saved under each Operator's personal classification to ensure optimal results, comfortable conditions and a safe treatment. All this is illustrated on a menu driven wide colour graphic display, making this system very user-friendly.

In this specification, the term "Electrolysis" is intended to mean a method of permanently removing superfluous or unwanted hair, wherein a fine needle is inserted into the hair follicle, an electric current is applied through the needle and destroys the hair root, or papilla, and the hair is removed. This includes the techniques known as galvanic thermolysis, RF, shortwave, diathermy, and BLEND™. The term "probe" should be understood as being any surgical instrument used to explore a wound or body cavity such as a needle.

BRIEF DESCRIPTION OF THE DRAWINGS

Further features and advantages of the present invention will become apparent from the following detailed description, taken in combination with the appended drawings, in which.

It will be rioted that throughout the appended drawings, like features are identified by like reference numerals.

DETAILED DESCRIPTION OF THE PREFERRED EMBODIMENT

Figure 1:
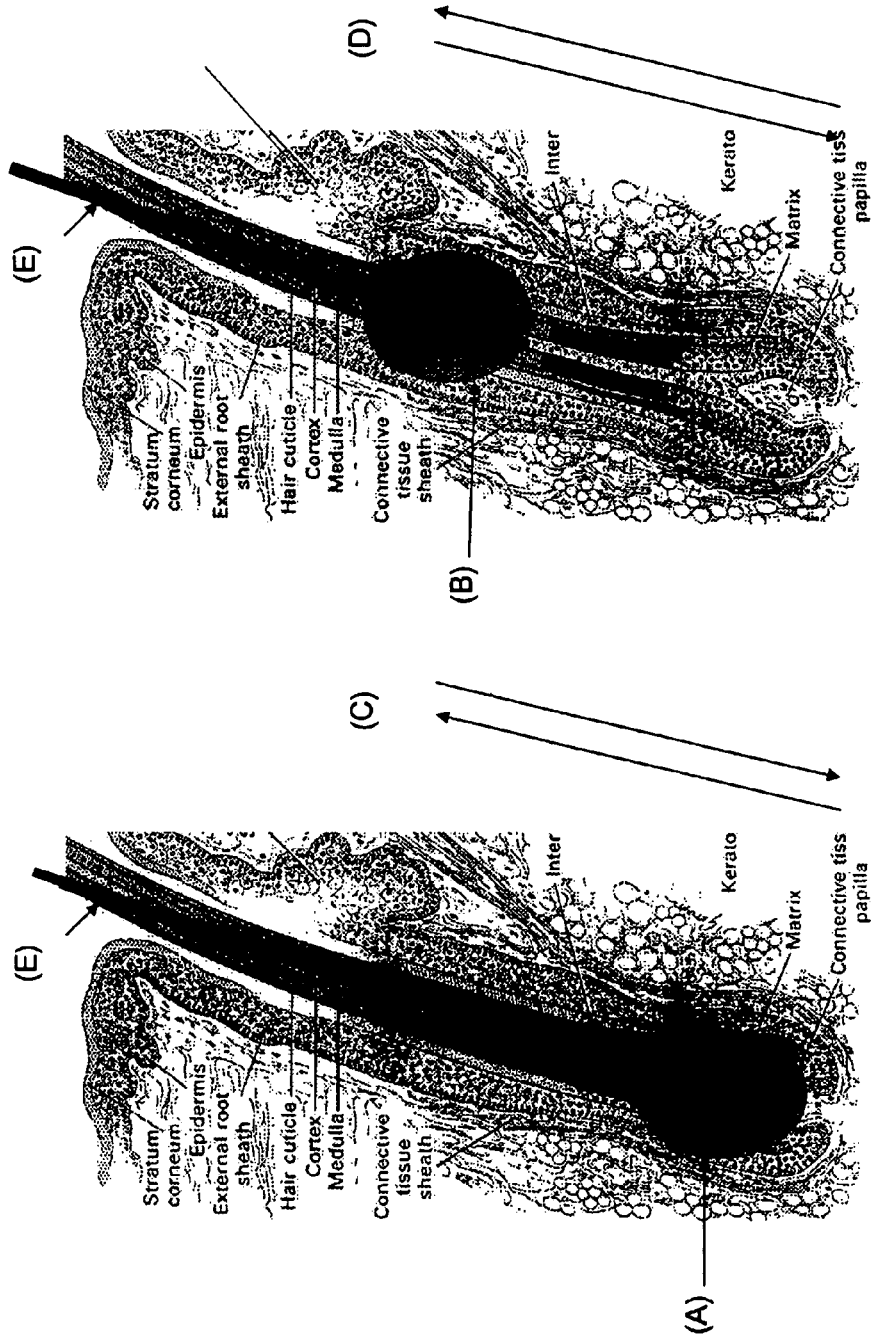
FIGS. 1a and 1b are cross-sectional view of a hair follicle with arrows showing the movement of the probe.

FIGS. 1a and 1b illustrate a standard hair follicle in the anagen phase (i.e. the growth phase of the hair cycle during which new hair is formed). FIG. 1a identifies the area (A) which includes the bulb region and FIG. 1b identifies the area (B) which includes the bulge region. The arrows (C) in FIG. 2a demonstrate the movement of an insulated probe (E) from the bulb region (A) to the bulge region (B) and back to the bulb region (A) with continuous heat. The arrows (D) in FIG. 1b show the process in the reverse direction, where the insulated probe (E) begins at the bulge region (B), moves down to the bulb region (A) and then back to the bulge region (B). The bulge region (B) is typically approximately ⅔ of the way up the hair follicle from the bottom and therefore, the displacement of the probe happens in this area.

It should be noted that while this example illustrates the hair follicle in the anagen phase, the method can also be done while the hair follicle is in the catagene or telogene phase, as will be understood by a person skilled in the art.

Figure 2:
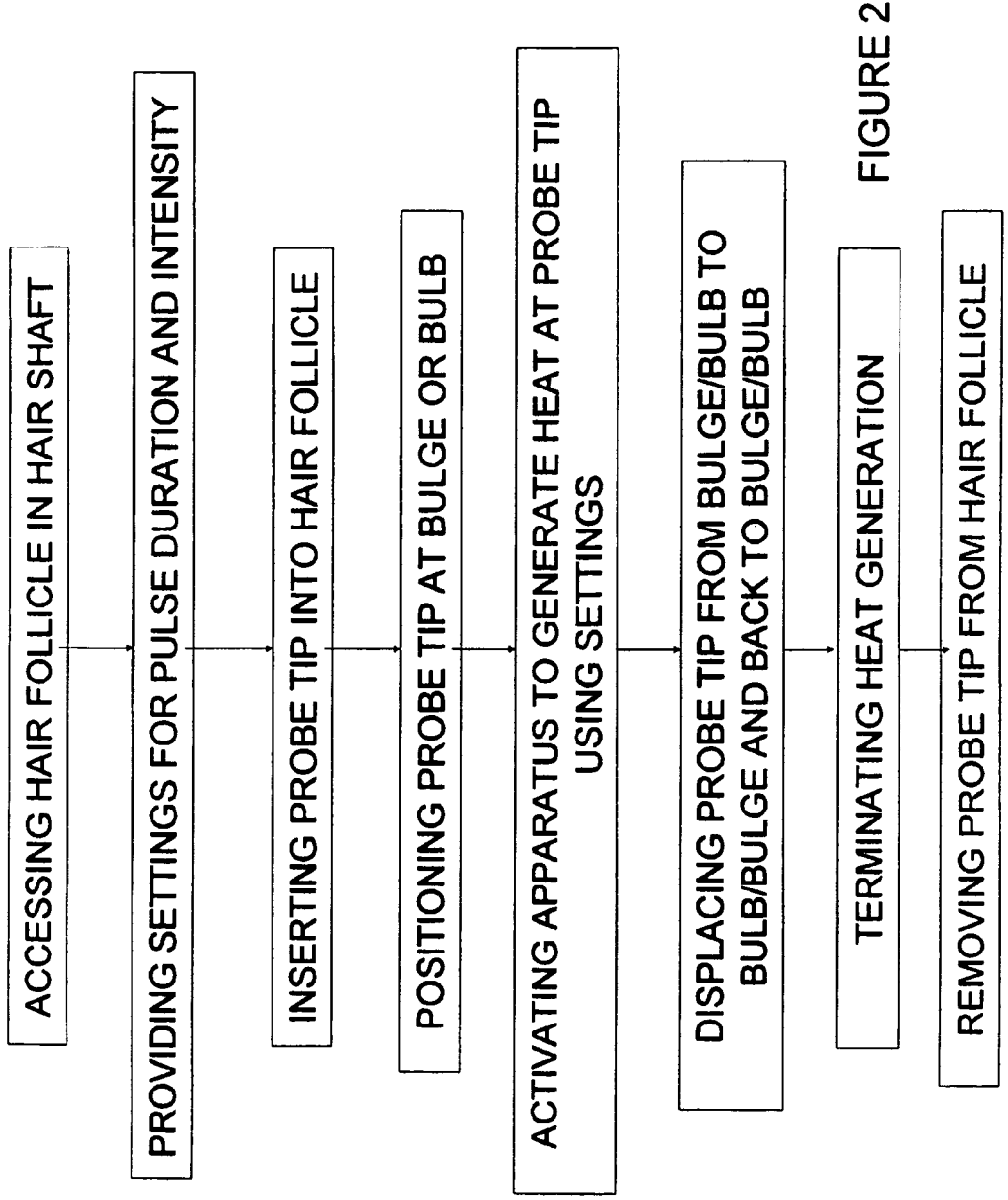
FIG. 2 is a flow-chart of one embodiment of the method of the present invention.

The method of epilation of the present invention is performed while using an insulated probe connected to an epilator apparatus supplying multiple pulses of energy that create concentrated heat at the probe tip. FIG. 2 is a flow chart illustrating the steps of the method. The first step consists in obtaining access to a hair follicle of a hair shaft, the hair follicle having a bulge containing germinating cells responsible for hair growth, and a bulb surrounding a papilla nourishing the follicle. Pulse duration and intensity settings defining at least a one way time equivalent to the time it takes to move the insulated probe from the bulb to the bulge or from the bulge to the bulb are provided to the apparatus. The probe tip is inserted into the hair follicle and positioned at a position corresponding to either the bulb or the bulge. The apparatus is then activated in order to generate heat at the probe tip using the predetermined settings. The probe tip is displaced from its initial position (at either the bulb or the bulge) to the other one of the bulb or the bulge. During this displacement, heat is continuously generated by applying multiple pulses of energy at the probe tip. The heat generated is sufficient to create a concentrated coagulation only at the tip of the insulated probe in order to destroy at least some of the germinating cells responsible for hair growth. When the predetermined duration has been reached, the generation of heat is terminated and the probe tip is removed from the hair follicle. At this point, removal of the hair with a pair of tweezers should not be met with any resistance from the hair.

In an alternative embodiment, the apparatus used with the method automatically detects that the probe has touched the skin outside the hair follicle and begins activation at a predetermined time after the detection. This function is performed by a sensor connected to the probe and to the central processing unit of the apparatus.

In a preferred embodiment, the predetermined settings for pulse duration and intensity define a total time it takes to move the insulated probe from the bulb/bulge to the bulge/bulb and back to the bulb/bulge. The displacement, which includes the back-and-forth movement, results in a plurality of pulses of energy being applied to the tip of the probe.

Also in a preferred embodiment, the hair follicle is in the anagen phase and the bulb surrounds the connective papilla. All germinating cells can then be destroyed.

Preferably, the insulated probe delivers the same pattern of coagulation to the bulge and bulb areas. At the same time, the probe protects the surface of the epidermis from reaction when moving within the follicle. This makes the whole process very comfortable for the patient receiving the epilation treatment. If a regular non-insulated probe were used, the pattern of coagulation would not be strong enough when placed at the bulb area and would increase when moving the probe toward the bulge area, thereby creating an epidermis reaction and causing pain in the process.

Presently, most conventional epilators on the market today uses a frequency of 13.56 MHz to destroy the hair follicle. The method of the present invention is used with an apparatus operating at a frequency ranging from 26.957 MHz to 27.283 MHz in a preferred embodiment. This frequency produces an electro-coagulation of tissues concentrated at the tip of the probe. The higher frequency and the stronger power lead to faster results. In addition, better concentration of destruction means less diffusion in the tissues and results in improved comfort for the patient. The method of the present invention is not limited to a frequency of approximately 27 MHz and can be used with alternative frequencies.

The method of the present invention can be used with various types of electrolysis, such as 27 MHz thermolysis, which is an apparatus that functions at radio frequencies. The three modes available under thermolysis are PICOFLASH™ PICOFLASH™ (pulses in thousandths of a second), MULTIPLEX™ (mixture of slow and quick pulses), and SYNCHRO™ (many hundred pulses in less than a thousandth of a second each). Another type of electrolysis is using galvanic currents, which is a single probe electrolysis. The BLEND™ type, which combines galvanic and thermolysis, is also feasible. There are a variety of modes available with BLEND™, and some of them are PULSING-BLEND™ technique, OMNI-BLEND™ technique, MULTI-BLEND™ technique, EVOLU-BLEND™ technique, and PICO-BLEND™.

PICO-BLEND™ is similar to PULSING-BLEND™. The galvanic current produces the chemical reaction while the RF pulses warm-up the lye to be more reactive. The 27 MHZ pulses are evenly distributed during the process. The RF level must be at a low level to prevent dehydration of the follicle. A possible selection of the first current to flow is Glv/RF.

OMNI-BLEND™ refers to the omni-presence of both currents. The RF level is adjusted to a low level to prevent dehydration of the follicle. With a regular probe, the chemical reaction may reach the surface after a few seconds, but with the use of a special insulated probe for blend, the chemical reaction will not be produced at the skin surface. A possible selection of the first current to flow is Glv/HF.

EVOLU-BLEND™ is a blend with an evolving action. The galvanic current will progress until it reaches its maximum level adjusted or programmed in the settings. The chemical reaction evolves while the RF current is controlled at a low level. EVOLUBLEND™ is similar to the Tolerance Test, known to a person Skilled in the art, but the RF 27 MHZ is added in a continuous manner to enable the epilation of the hair. When blending both currents more caustic soda is produced from the base of the probe.

MULTI-BLEND™ combines OMNI-BLEND™ and MULTIPLEX™ techniques, while applying PICOFLASH™ pulses. This produces better and faster blend results. The MULTI-BLEND™ technique completes the blend with a final coagulation that spreads rapidly throughout the area developed by the caustic soda.

In addition, the method of the present invention may be used with at least two iontophoresis modes, which means using an electric current to introduce the ions of a medicament into bodily tissues.

IsoBlend™ and IsoGard™ are two types of insulators that can be used with the probe. The IsoGard™ insulated probe produces a narrow pattern of intensity at the tip of the probe, while the IsoBlend™ insulated probe produces a wider pattern when the power is increased. Too much intensity may cause a "blow out" effect and adjustment of the intensity is advised. The non-insulated area of the probe is important to enable the chemical reaction. Concentration of lye production is at the base of the follicle.

Figure 3:
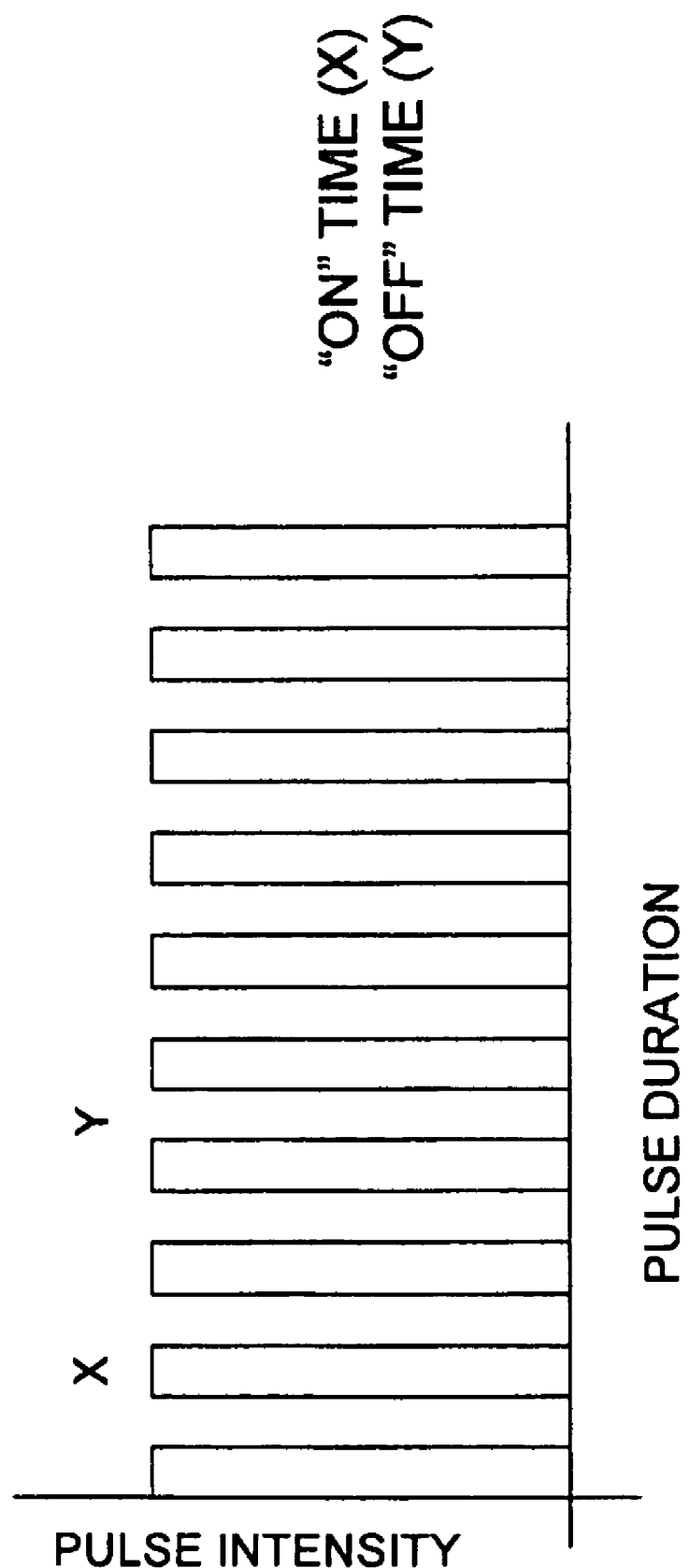
FIG. 3 is a graph of pulse duration versus pulse amplitude for one embodiment of the present invention.

FIG. 3 illustrates one embodiment of the total time in seconds that the probe is on versus the amplitude of a series of pulses applied to the probe. In this example, the "on" time (X) of the probe is equivalent to the "off" time of the probe. Alternatively, the "on" time of the probe may be different than the "off" time of the probe. A plurality of pulses of equal amplitude and equal duration are applied to the hair follicle during the process. The delay between the pulses is adjustable with more or less resting time and the total displacement time, which has to be set according to the electrologist's displacement speed. This will lead to more localized destruction from the bulb to the bulge area.

The various modes of the apparatus can be combined when using the method of the present invention. For example, a first process of RF at low intensity, where heat enhances electrical conductivity in the follicle, can be followed by a second process with PICOFLASH™. During PICOFLASH™, coagulation will be concentrated at the tip of the probe and the heat will penetrate better. Alternatively, a MULTIPLEX warming process is combined with PICOFLASH™. The first low-power RF pulse produces a porous effect in the follicle. The second PICOFLASH™ pulse produces a quick coagulation with a strong pattern of destruction. This may be used with PICOFLASH™ Proportional Pulsing (PPP). This is especially ideal for coarse hair or slightly distorted follicles. Proportional pulsing with displacement reduces the duration of each pulses and leads to adjustability of the delay between pulses.

Synchronized multiple PICOFLASH™ pulses lead to tiny coagulation concentrated at the tip of the probe. This mode is combined with slight movement from the bulb to the bulge to the bulb to cause a destruction of all cells in the lower 2-3 area of the follicle.

A SYNOCHRO™ modality, which involves multiple PICOFLASH™ with the ISOGARD™ probes can also be used. Very fast pulses at a medium intensity level and synchronized bulb-bulge and/or bulge-bulb displacement give positive results.

In accordance with the present invention, the apparatus used with the method of the present invention may receive smart cards having prepaid electrolysis time on them. The card may include data allowing validation of a salon's identification number and a certain number of minutes for a treatment, such as 150, 300 and 600 minutes. When a treatment is done, the number of minutes used for the treatment are automatically deducted from the smart card. General client information may also be stored on the card. The smart card may be used to increase client fidelity and increase a salon's cash flow. Cards can be available as gift certificates and will serve to compete with laser epilation services which are sold in packages.

The apparatus used with the method of the present invention may have an internal memory for storing client information, such as names, frequency of visits, preferences, specific settings of the client, etc. This machine also allows the generation of statistics per body areas, per mode used, per client, etc. The machine may also print out session reports, cumulative sales reports, client lists with statistics, etc.

Figure 4:
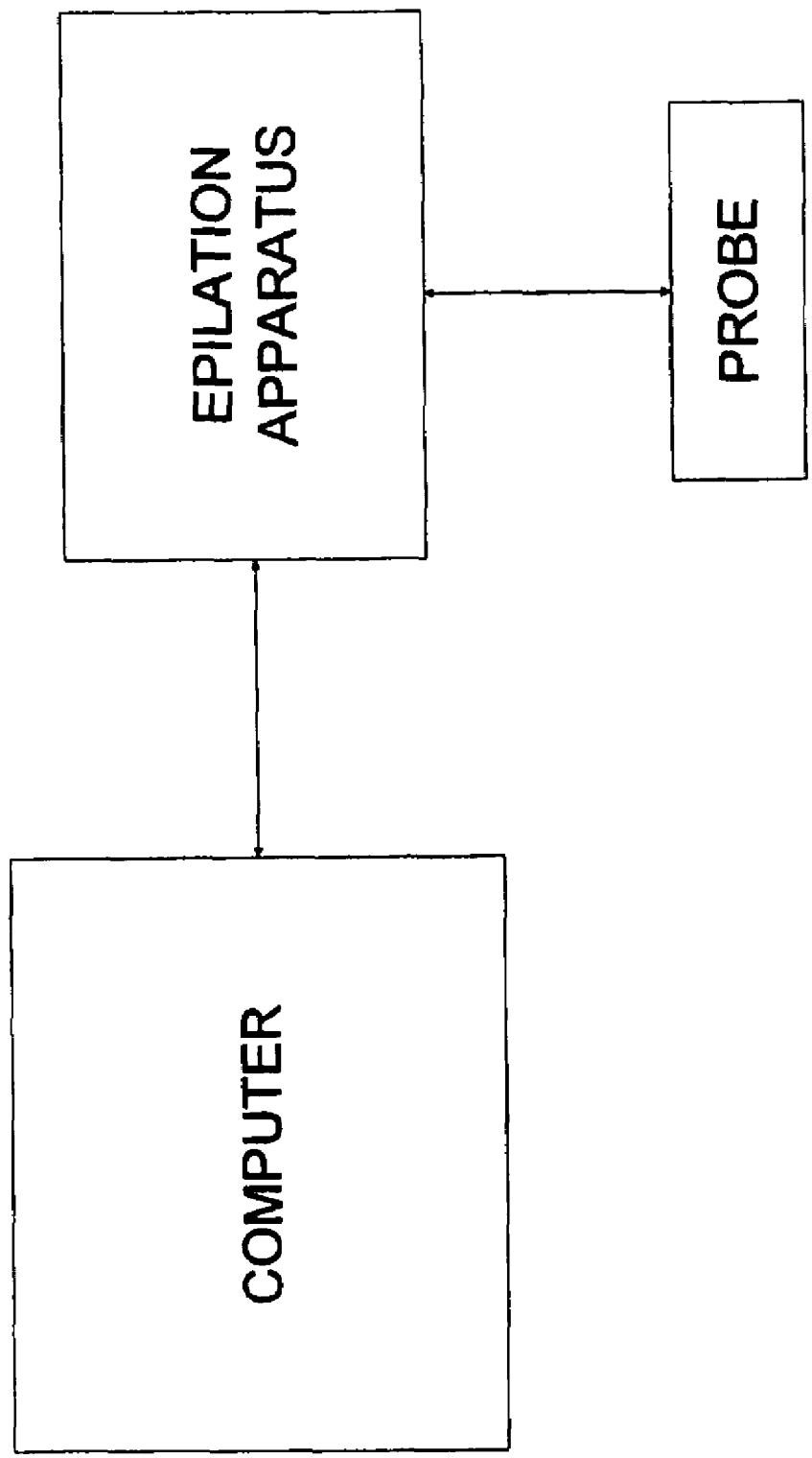
FIG. 4 is a block diagram of one embodiment of an apparatus used with the method of the present invention.

The apparatus may be connected to a computer in various ways, as illustrated in FIG. 4, such as using an RS-232 connection with the appropriate software, for example, ALPHA SALON™ software. The computer software may allow updates of file histories for individual clients, can transfer electrolysis charges to the computer, and can generate prepaid smart card reports. A wireless connection between the apparatus and a computer is also possible.

The program settings for the different processes may be created on and provided by the computer. The settings can then be transferred to the apparatus upon request by the machine or by a manual operation made on the computer directly. The computer can store all of the information used by the apparatus and transfer it when necessary.

The embodiments of the invention described above are intended to be exemplary only. The scope of the invention is therefore intended to be limited solely by the scope of the appended claims.

I claim:

1. A method of epilation using an insulated probe connected to an epilator apparatus supplying multiple pulses of energy that create concentrated heat at the probe tip comprising the steps of:
    obtaining access to a hair follicle of a hair shaft, said hair follicle having a bulge providing germinating cells responsible for hair growth, and a bulb surrounding a papilla nourishing the follicle;
    providing pulse duration and intensity settings to said apparatus, said pulse duration and intensity settings defining at least a one way time equivalent to a time taken to move the insulated probe from one of the bulb to the bulge and the bulge to the bulb;
    inserting said probe tip into said hair follicle;
    positioning said probe tip at a position corresponding to one of the bulb and the bulge;
    activating said apparatus to generate heat at the probe tip using said settings;
    displacing said probe tip from the position to the other of the bulb and the bulge with continuous generation of heat using the multiple pulses of energy at the probe tip, wherein said heat is sufficient to create a concentrated coagulation only at the tip of the insulated probe to destroy at least some germinating cells responsible for hair growth, a total time being determined by a speed of movement of the probe tip by an operator of the probe in a ⅔ lower portion of the follicle;
    terminating said generation of heat; and
    removing said probe tip from said hair follicle.

2. A method as claimed in claim 1, wherein said displacing comprises also displacing said probe tip back to said position.

3. A method as claimed in claim 1, wherein the hair follicle is in the anagen phase and the bulb surrounds the connective papilla.

4. A method as claimed in claim 1, wherein said destroying destroys all germinating cells.

5. A method as claimed in claim 1, wherein said epilation is done using one of Thermolysis and Blend.

6. The method as claimed in claim 1, wherein the duration of each pulse may be adjusted to a very short "on" time x calculated in microseconds and a very short "off" time y calculated in microseconds.

7. The method as claimed in claim 1, wherein the epilation apparatus is a thermolysis epilation apparatus and said energy is supplied by a radio wave of 27 MHz which offers a more condense coagulation process which in turn has a more comfortable treatment than a conventional epilator.

8. The method of claim 1, wherein said settings are provided by selecting a mode on said apparatus for retrieving said settings.

9. The method of claim 1, wherein said settings are provided by manually entering said settings using an operator interface.

10. The method of claim 1, wherein said settings are registered onto a client smart card and provided by inserting said client smart card into a card reader able to communicate with said epilation apparatus.

11. The method of claim 10, wherein said card reader is provided within said epilation apparatus.

12. The method of claim 10, wherein said card reader is provided on a computer used to manage epilation of a plurality of clients and able to communicate with said epilation apparatus.

13. The method of claim 1, wherein said settings can be stored and retrieved for data monitoring and statistics.

14. The method of claim 10, further comprising a step of automatically detecting that said probe has touched the skin outside said hair follicle and beginning said activating at a predetermined time after said detection.

15. The method of claim 1, wherein said settings are created on and provided by a computer used to manage epilation of a client and able to communicate with said epilation apparatus.

* * * * *